United States Patent [19]

Huang

[11] Patent Number: 4,866,173

[45] Date of Patent: Sep. 12, 1989

[54] THERAPEUTIC SUBSTITUTED SEMICARBAZIDES

[75] Inventor: Fu-chih Huang, Boonton, N.J.

[73] Assignee: Rorer Pharmaceutical Corporation, Fort Washington, Pa.

[21] Appl. No.: 125,764

[22] Filed: Nov. 23, 1987

Related U.S. Application Data

[63] Continuation of Ser. No. 627,489, Jul. 5, 1984, abandoned, which is a continuation of Ser. No. 421,701, Sep. 22, 1982, abandoned.

[51] Int. Cl.$^4$ .................. C07D 237/08; C07D 223/06; C07D 401/00; C07C 133/02
[52] U.S. Cl. .................................... 544/224; 540/598; 544/238; 560/34; 560/121; 548/533; 546/147; 546/309; 562/560; 562/443
[58] Field of Search .................. 544/224, 238; 560/34, 560/38; 540/598

[56] References Cited

U.S. PATENT DOCUMENTS

| | | | |
|---|---|---|---|
| 4,374,829 | 2/1983 | Harris et al. | 260/112.5 R |
| 4,610,816 | 9/1986 | Berger | 549/452 |
| 4,634,715 | 1/1987 | Greenlee et al. | 514/423 |
| 4,725,608 | 2/1988 | Nakaguchi et al. | 544/224 |

FOREIGN PATENT DOCUMENTS

| | | |
|---|---|---|
| 54862 | 6/1982 | European Pat. Off. . |
| 58918 | 9/1982 | European Pat. Off. . |

OTHER PUBLICATIONS

Burger, *Medicinal Chemistry*, 2nd ed., (1960), pp. 42–43.

*Primary Examiner*—Mukund J. Shah
*Assistant Examiner*—E. Bernhardt

[57] ABSTRACT

There are disclosed semicarbazides having antihypertensive and angiotensin converting enzyme inhibitory activity.

3 Claims, No Drawings

THERAPEUTIC SUBSTITUTED SEMICARBAZIDES

This application is a continuation of previously copending application Ser. No. 627,489, filed July 5, 1984, which, in turn, is a continuation of application Ser. No. 421,701, filed Sept. 22, 1982, both now abandoned.

This invention relates to new substituted semicarbazides, having valuable pharmacological activity It particularly relates to semicarbazide compounds having antihypertensive and angiotensin converting enzyme inhibitory activity and the structure

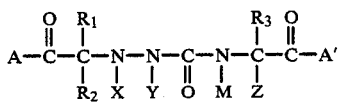

wherein

A and A' are independently hydroxy, alkoxy, alkenoxy, dialkylamino alkoxy, acylamino alkoxy, acyloxy alkoxy, aryloxy, aralkyloxy, amino, alkanoylamino, alkylamino, dialkylamino, hydroxyamino; or substituted aryloxy or aralkoxy wherein the substituent is alkyl, halo, or alkoxy;

$R_1$ is hydrogen; alkyl, alkenyl or alkynyl containing from 1 to 20 carbon atoms; cycloalkyl; aryl; heterocyclic; fused aryl-cycloalkyl; aralkyl; substituted alkyl, alkenyl and alkynyl wherein the substituent is halo, hydroxy, alkoxy, aryloxy, amino, alkylamino, dialkylamino, acylamino, arylamino, guanidino, imidazolyl, indolyl, mercapto, alkylthio, arylthio, carboxy, carboxamido, or carboalkoxy; aryl; substituted aryl wherein the substituent is lower alkyl, alkoxy or halo; aralkyl; heterocyclicalkyl; aralkenyl or heterocyclicalkenyl; substituted aralkyl, heterocyclicalkyl, aralkenyl, or heterocyclicalkenyl wherein the substituent is halo, dihalo, alkyl, hydroxy, alkoxy, amino, aminoalkyl, acylamino, dialkylamino, alkylamino, carboxy, haloalkyl, cyano or sulfanyl; aralkyl or heterocyclicalkyl substituted on the alkyl moiety by amino or acylamino;

$R_2$ and $R_3$ are independently hydrogen, alkyl, alkenyl, alkynyl, aralkyl or cycloalkyl;

M is hydrogen, alkyl, alkenyl, alkynyl, cycloalkyl, cycloalkyl-alkyl, polycycloalkyl, polycycloalkyl-alkyl, aryl, aralkyl, heteroaryl, heteroaryl-alkyl, heterocycloalkyl, heterocycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkyethioalkyl, alkylaminoalkyl, dialkylaminoalkyl;

Z is hydrogen, alkyl, cycloalkyl, phenyl, phenylalkyl, hydroxyphenylalkyl, hydroxyalkyl, aminoalkyl, guanidinoalkyl, imidazolylalkyl, indolylalkyl, mercaptoalkyl, or alkylthioalkyl;

M and Z when taken together form an alkylene bridge of from 2 to 4 carbon atoms; an alkylene bridge of from 2 to 3 carbon atoms and one sulfur atom; an alkylene bridge of from 3 to 4 carbon atoms containing a double bond; a substituted alkylene bridge containing 2 to 5 carbons in which the substituent is hydroxy, lower alkoxy, or lower alkyl; fused aralkylene; or fused heteroaralkylene;

M and Z when taken with the carbon and nitrogen to which they are respectively attached form a tetrahydroisoquinoline; dihydroindole or pyrrolidine ring;

X is hydrogen, alkyl, aryl, heteroaryl, aralkyl or acyl;

Y is hydrogen, alkyl, aminoalkyl, aryl, alkylaminoalkyl, arylaminoalkyl, mercaptoalkyl, aralkyl or heteroarlyalkyl;

X and Y when taken together form an alkylene bridge of from 2 to 5 carbon atoms; an alkylene bridge of from 2 to 3 carbon atoms and one sulfur atom; an alkylene bridge of from 3 to 4 carbon atoms containing a double bond; a substituted alkylene bridge containing 2 to 5 carbon atoms in which the substituent is hydroxy, alkoxy, alkyl; or fused aralkylene or heteroaralkylene.

The alkyl groups in alkyl per se, aralkyl, alkoxy, aminoalkyl, thioalkyl, haloalkyl, and hydroxyalkyl are preferably lower alkyl containing 1 to 6 carbon atoms and may be branched or straight chain.

The alkenyl and alkynyl groups contain from 2 to 6 carbon atoms and may be branched or straight chain.

The alkyl, alkenyl, and alkynyl groups may be substituted with substituents such as hydroxy, alkoxy, halo, amino, alkylamino, mercapto and alkylmercapto.

The cycloalkyl and cycloalkyl groups contain from 3 to 7 carbon atoms in the ring. Such cycloalkyl groups may be substituted with substituents such as alkyl, halo, haloalkyl, hydroxy, hydroxyalkyl, alkoxy, amino, aminoalkyl, alkylamino, trifluoromethyl, and nitro.

The aryl groups may have from 6 to 10 carbons and include phenyl and α- and β-naphthyl. The aryl groups may contain substituents such as alkyl, hydroxy, alkoxy, hydroxyalkyl, mercapto, alkylmercapto, mercaptoalkyl, halo, haloalkyl, amino, alkylamino, aminoalkyl, nitro, methylenedioxy, trifluoromethyl, ureido, and guanidino.

The fused aryl-cycloalkyl comprise phenyl rings fused to cycloalkyl rings having from 3 to 7 carbon atoms. These groups also include fused aryl-cycloalkyl-alkyl.

The heterocyclic group per se, and in the heterocyclicalkyl and fused rings may be saturated, partially saturated or unsaturated and includes such groups as pyridinyl, piperidinyl, morpholinyl, pyrrolyl, pyrrolidinyl, thiomorpholinyl, quinolinyl, isoquinolinyl, tetrahydroquinolinyl, thiazolidinyl, thiazolinyl, thiazolyl, imidazolidinyl, imidazolinyl, imidazolyl, thiophenyl, tetrahydrothiophenyl, furyl, tetrahydrofurayl, and the like. These heterocyclic groups may also contain substituents as described from the aryl groups above. The heterocyclic group also includes heterocyclic lower alky.

The halo substituents include fluorine, chlorine, bromine and iodine.

Preferred compounds are those wherein X and Z are each hydrogen, Y is hydrogen, alkyl, aminoalkyl, mercaptoalkyl, arylaminoalkyl, imidazoalkyl, indolylalkyl, cycloalkyl or aralkyl, as well as compounds in which X and Y are as defined and Z and M taken together form an alkylene bridge of 2 to 4 carbon atoms which may be interrupted by a sulfur atom, or contain a double bond, or be substituted with substituents such as hydroxy, lower alkoxy or lower alkyl; or a fused aralkylene or heteroaralkylene. Additional preferred compounds include those in which M and Z together with the C and N to which they are attached form a tetrahydroisoquinoline, dihydroindole or pyrrolidine ring.

Particularly preferred compounds are those in which M is indanyl, tolyl, cycloalkyl, or heterocyclic; $R_1$ is indanyl or phenethyl; and M and Z together with the C and M to which they are attached form a tetrahydroisoquinoline, dihyroindole or pyrrolidine ring.

Suitable acid addition salts include inorganic salts such as hydrochloride, phosphate and sulfate; organic carboxylates such as acetate, malate, maleate, fumarate, succinate, citrate, lactate, benzoate, hydroxybenzoate, aminobenzoate, nicotinate, and the like, and organic sulfonic and phosphonic acids such as toluenesulfonic acid.

Suitable basic salts include alkali and alkaline earth metal salts such lithium, sodium, potassium, magnesium and calcium and iron, as well as ammonium and quarternary ammonium salts.

It is to be understood that the compounds of the present invention may have one or more asymmetric carbon atoms and the various racemic mixtures as well as the individual optically active compounds are considered to be within the scope of the present invention.

The compounds of this invention can be prepared by condensation under dehydrating and reducing conditions of a hydrazine compound of the formula:

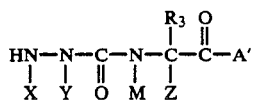
II with an alpha keto acid derivative of the formula:

III to form compounds in which $R_2$ and X are hydrogen; or condensing compounds of formula II with an alpha-haloacid derivative of the formula:

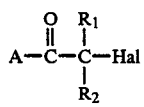
IV under conditions for removal of hydrogen halide.

Additionally, the present compounds can be prepared by acylating a hyrdazine compound of the formula:

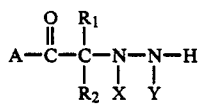
V with a halogen compound of the formula:

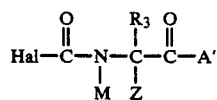
VI under conditions for removal of hydrogen halide.

Alternately, the compounds of this invention can be prepared by reduction of the corresponding azo compound to provide products in which X and Y are hydrogen.

Compounds of structures II-IV can be prepared by art-recognized procedures. For example, compounds of structure VI by reaction of phosgene with compounds of the following formula:

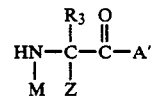
VII

Compounds of structure III include known compounds as do compounds of structure IV.

The foregoing reactions are carried out in organic solvents such as acetonitrile, tetrahydrofuran, dioxane, lower alkanols, acetic acid, methylene chloride, ethylene chloride and similar such solvents. Most reactions occur readily at room temperature and some preferably at lower than room temperature, down to 0° C. As with many organic chemical reactions, the use of higher temperatures usually results in shorter reaction times. Thus, even where initial reactions are conveniently conducted at room temperature or lower temperature, the use of higher temperatures after the initial reaction subsides where exothermic, can increase the yields of product obtained. Conveniently, reaction mixtures can be digested at reflux temperature of the mixture.

In those reactions where hydrogen halide is formed, it is preferred to employ hydrogen halide acceptors as is well-known in this art. In the present processes, any of the usual hydrogen halide acceptors can be employed, e.g., triethylamine, picolines, pyridine and other tertiary organic amines, as well as various inorganic bases such as metal carbonates and bicarbonates e.g. $NaHCO_3$, $CaCO_3$ and $K_2CO_3$.

The aforesaid condensation, dehydration and reducing conditions for reaction of compounds of structure II with those of structure III can be conveniently accomplished in the same reactor as a combined reaction in separate stages. The condensation and dehydration steps result in a compound of the formula:

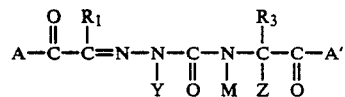

which is then reduced to the corresponding dihydro compound of formula I.

The dehydration reaction can be conducted using standard dehydrating agents such as dehydrating silica gels, acids such as toluenesulfonic acid, solvents which form azeotropes with water, such as benzene and toluene, and similar dehydrating agents. The condensation and dehydration steps are normally simultaneously effected, generally in a solvent such as those mentioned hereinbefore, conveniently at room temperature, although temperatures from 0°-reflux temperature, of the mixture can be used. Of course, when an azeotropic removal of water is accomplished using a suitable solvent, reflux temperature is used and water is removed by a suitable trap, e.g., Dean-Stark apparatus.

The reduction reaction can be accomplished without isolation of the dehydration product by addition of a suitable reducing agent either after the dehydration or simultaneously with the dehydrating agent. Suitable reducing agents include, of course, noble metal catalysts with hydrogen gas, usually at room temperature and moderate pressures of hydrogen gas, or chemical reducing agents such as metals and mineral acids, e.g. zinc and hydrochloric acid, or metal hydrides such as borohydrides or aluminohydrides, e.g. sodium cyanoborohydride.

After the desired reaction step is accomplished the final product is recovered by usual methods from the reaction mixtures in which produced and thereafter purified, e.g., by chromatography such as column chromatography or gas-liquid chromatography, or by recrystallization from suitable solvents.

Various substituents on the present new compounds, e.g., as defined for $R_1$, can be present in the starting compounds or added after formation of the products by the known methods of substitution or conversion reactions. Thus, the nitro group can be added to the final product by nitration of the aromatic ring and the nitro group converted to other groups, such as amino by reduction, and halo by diazotization of the amino group and replacement of the diazo group. Other reactions can be effected on the formed product. Amino groups can be effected on the formed product. Amino groups can be alkylated to form mono and dialkylamino groups, mercapto and hydroxy groups can be alkylated to form corresponding ethers. Thus, substitution or alteration reactions can be employed to provide a variety of substituents throughout the molecule of the final products. Of course, reactive groups where present should be protected by suitable blocking groups during any of the aforesaid reactions particularly the condensation reactions.

The acid and base salts of the present new compounds can be formed using standard procedures. Often they are formed in situ during the preparation of the present new compounds.

The present compounds obviously exist in stereoisomeric forms and the products obtained thus can be mixtures of the isomers, which can be resolved. Alternatively, by selection of specific isomers as starting compounds, the preferred stereoisomer can be produced. Therefore, the preferred forms, where each asymmetric center (chiral center) is in the S-configuration, are preferably prepared by the stereospecific route rather than attempting resolution of mixtures of isomers. The compounds in which the S-configuration exists at all asymmetric centers are the most active; those in which the R-configuration exists are of less activity; and those where both R- and S-configuration exist are of intermediate activity.

EXAMPLE 1

A. N-(1-Methyl-1 hydrazinocarbonyl)-proline t-butyl ester

A mixture of proline t-butyl ester (5.1 g) and triethylamine (3 g) in 50 ml of $CH_2Cl_2$ was added dropwise to phosgene (3 g) in 50 ml of $CH_2Cl_2$ in a icebath. The reaction mixture was stirred for 10 minutes and was then added dropwise to a solution of methylhydrazine (1.3 g) and triethylamine (3 g) in 50 ml of methylene chloride at 0°. The reaction mixture was stirred for an additional 30 minutes. The organic solution was washed with 1 N NaOH solution, water, dried and evaporated to give 5 g of crude product. Purification by dry column chromatography gave 2 g of desired product.

B. N-[1-Methyl-2-(1-ethoxycarbonyl-3-phenylpropyl)-hydrazinocarbonyl] proline t-butyl ester A solution of the product from A (1.8 g), 6.31 g of ethyl benzylpyruvate and 10 g of molecular sieve (4 A) in 50 ml of absolute ethanol was stirred at room temperature for one hour. Then 0.6 g of sodium cyanoborohydride was added and stirring was continue=d overnight. After filtration and evaporation of solvent the residue was dissolved in $Na_2CO_3$ to pH 10, the aqueous solution was extracted with ethyl acetate and the combined extracts dried over magnesium sulfate, and then concentrated. Purification with dry column chromatography gave 0.9 g of product.

EXAMPLE 2

N-[1-Methyl-2-(1-ethoxycarbonyl-3-phenylpropyl)hydrazinocarbonyl] proline

A solution of 0.4 g of the product of Example 1 in 50 ml anhydrous ether was treated with dry HCl gas at 0° C. for two hours. Solvent was evaporated to dryness. Purification of the crude product through Dowex 50 X 2-100, resin gave 0.3 g of product.

EXAMPLE 3

In the same manner as described in Examples 1 and 2 the following compounds are prepared:

N-[1-Methyl-2-(1-ethoxycarbonyl-3-phenylpropyl)hydrazinocarbonyl]-N-p-tolylglycine t-butyl ester (oil)

N-[1-Methyl-2-(1-ethoxycarbonyl-3-phenylpropyl)hydrazinocarbonyl]-N-p-tolylglycine (oil)

N-[1-Methyl-2-(1-ethoxycarbonyl-3-phenylpropyl)hydrazinocarbonyl]-N-(5-indanyl)glycine t-butyl ester (oil)

N-[1-Methyl-2-(1-ethoxycarbonyl-3-phenylpropyl)hydrazinocarbonyl]-N-(5-indanyl)glycine (semisolid, hydroscopic)

N-[1-Methyl-2-(1-ethoxycarbonyl-3-phenylpropyl)hydrazinocarbonyl] 1,2,3,4-tetrahydro-3-carboxyisoquinoline N-[1-(4-Aminobutyl)-2-(1-ethoxycarbonyl-3-phenylpropyl)hydrazinocarbonyl] proline N-[1-(4-Aminobutyl)-2-(1-ethoxycarbonyl-3-phenylpropyl)hydrazinocarbonyl]-N-(5-indanyl)glycine N-[1-Methyl-2-(1-ethoxycarbonyl-3-phenylpropyl)hydrazinocarbonyl]-N-p-tolyl-glycine N-[1-Methyl-2-(1-ethoxycarbonyl-3-phenylpropyl)hydrazinocarbonyl]-N-(5-indanyl)glycine N-[1-Methyl-2-(1-ethoxycarbonyl-3-phenylpropyl)hydrazinocarbonyl]proline tertiary butyl ester N-[1-Methyl-2-(1-ethoxycarbonyl-3-phenylpropyl)hydrazinocarbonyl]-N-(5-indanyl)glycine tertiary butyl ester N-[1-Methyl-2-(1-ethoxycarbonyl-3-phenylpropyl)hydrazinocarbonyl]-1,2,3,4-tetrahydroisoquioline-3-carboxylic acid N-[1-Methyl-2-(1-ethoxycarbonyl-3-phenylpropyl)hydrazinocarbonyl]-1,2,3,4-tetrahydroisoquinoline-3-carboxylic acid tertiary butyl ester.

N-[1-Methyl-2-(1-ethoxycarbonyl-3-phenylpropyl)hydrazinocarbonyl]-N-(2-indanyl)glycine tertiary butyl ester N-[Methyl-2-(1-ethoxycarbonylethyl)hydrazinocarbonyl]-N-(2-methylcyclopentyl)glycine N-[1-Benzyl-2-methyl-2-carboxymethylhydrazinocarbonyl]-N-(4-pyridyl)glycine diethylamide.

N-[1,2-bis(4-chlorophenyl)-2-(1-carboxybenzyl)hydrazinocarbonyl]phenylalanine ethoxyethyl ester.

N-[1-Ethyl-2-benzyl-2-(N,N-dimethylcarboxamidomethyl)hydrazinocarbonyl]-2,2-dimethylsarcosine. 1-(1-Ethoxycarbonylethyl))-2-carboxymethylaminocarbonylhexahydropyridazine.

EXAMPLE 4

N-Methyl-N'-(1-carbethoxyethyl)hydrazinocarbonyl-L-proline t-butyl ester

A mixture of N-(N'-methyl-N'-hydrazinocarbonyl)-proline t-butyl ester (0.4 g), ethyl pyruvate (9.65 g) and molecular sieve-type 4 Å (2 g) in absolute ethanol is stirred at room temperature for one hour and sodium cyanoborohydride (1.4 g) was added. The mixture is stirred at room temperature overnight. After removing solvent, the residue is slurried in water (~100 ml), made acidic (pH 2) with dilute hydrochloric acid and extracted with ethyl acetate (200 ml). The ethyl acetate extract was evaporated to dryness and the residue slurried in water (pH=10, with aqueous sodium hydroxide).

The product is extracted with ethyl acetate, dried and evaporated to yield 2.8 g oily product.

EXAMPLE 5

N-Methyl-N'-(1-carbethoxyethyl)hydrazinocarbonyl-L-proline hydrochloride

The product is dissolved in anhydrous ether and dry hydrogen chloride bubbled into the solution over a two hour period. The solution is evaporated to dryness to yield 1.3 g of the product as the hydrochloride salt.

As previously mentioned, the present new compounds exist in stereoisomeric forms due to asymmetric centers in the molecules where $R_3$ and Z as well as $R_1$ and $R_2$ differ. Such compounds can be obtained in their specific stereoisomeric forms by resolution procedures commonly employed for the purpose.

Alternatively, the use of stereospecific synthetic procedures can give a specific isomer as illustrated in the following example which describes production of an S,S isomer which is the preferred form of the present new compounds, having the most desirable therapeutic properties.

EXAMPLE 6

A. (S)-2-Benzylamino-4-phenylbutyric acid

A mixture of lg of (L)-2-amino-4-phenylbutyric acid, benzaldehyde (0.59 g) in 5.6 ml of 1N NaOH was stirred at room temperature for 30 minutes. The reaction mixture and 150 mg of 5 Pd/C was hydrogenated at 15 psi for 2 hours. After filtration, the reaction mixture was acidified to pH 4 to give 1 g of product.

B. (S)-Ethyl N-nitroso-2-benzylamino-4-phenylbutyrate

To a solution of ethyl 2-benzylamino-4-phenylbutyrate (0.7 g) in 4.8 ml of 1N HCl was added 0.2 g of sodium nitrite. The reaction mixture was heated at 80° C. for 1 hour, cooled, and then neutralized to pH 8. The reaction mixture was extracted with ethyl acetate. The organic solution was dried and evaporated to dryness. The crude product was purified by dry column chromatography to give 0.5 g of pure nitroso compound.

C. (S)-Ethyl 2-(N-benzyl-N'-acetyl)-hydrazino-4-phenylbutyrate

To a solution of the nitroso compound from B (5 g) in 20 ml of acetic acid-acetic anyhdride (3:1) was added slowly 10 g of zinc dust. The reaction mixture was stirred at room temperature overnight and then filtered. After evaporation of solvent, the crude product was purified by dry column chromatography to give 2 g of desired compound.

D. (S)-Ethyl 2-(N,N'-diacetyl)-hydrazino-4-phenylbutyrate

The compound obtained from C (0.4 g), 0.15 g of 5% Pd/C, and 1 ml of concd HCl in 100 ml of ethanol was hydrogentated at 50 psi for 3 hours. After filtration and evaporation of solvent, the residue was acetylated with acetic anhydride to give 0.2 g of desired compound.

E. (S)-Ethyl 2-(N'-methyl-N,N'-diacetyl)hydrazino-4-phenylbutyrate

The diacetyl compound (0.6 g) methyl iodide (2.25 g), and silver oxide (0.9 g) in 5 ml of DMF was stirred at room temperature overnight. After filtration, DMF was removed under reduced pressure. The residue was taken into methylene chloride and the organic solution was washed with 5% sodium cyanide solution, water and dried. After evaporation of solvent, the crude product was purified by dry column chromatography to give 0.2 g of pure product.

F. (S)-Ethyl 2-hydrazino-4-phenylbutyrate

The N-methyl compound obtained above (0.2 g) was refluxed with 10 ml of 6N HCl for 1 hour. After evaporation of water, the product was purified by Dowes 50-2X to give 60 mg of N-methyl-hydrazino-4-phenylbutyric acid, $[\alpha]_D = -6.7$.

The acid was esterified with ethanol-hydrogen chloride to give an ester as hydrochloride salt.

G. N-[1-methyl-2-(1-Ethoxycarbonyl-3-phenylpropyl)] hydrazinocarbonyl-proline t-butyl ester (S,S)

To a solution of the N-methyl compound obtained from F (0.67 g) and 0.66 g of triethylamine in 10 ml of methylene chloride was added 0.41 g of N-carbamoyl-chloride of L-proline t-butyl ester in 5 ml of methylene chloride at 0° C. The reaction mixture was stirred for 2 hours. After work-up, the crude product was purified to give 0.55 g of pure product, $[\alpha]_D = -30$.

N-[1-methyl-2-(-ethoxycarbonyl-3-phenylpropyl)]hydrazino carbonylproline (S,S)

The t-butyl ester (0.37 g) in 100 ml of ether was treated with hydrogen chloride at 0° C. for 3 hours. Evaporation of solvent gave the desired compound as hydrogen chloride salt, $[\alpha]_D = -19.4$.

Compounds of this invention demonstrate potent activity (e.g. of the order of $I_{50}$ of 100 micromols) in inhibiting the angiotensin converting enzyme (ACEI activity) when tested by the method described in Science 196, 441-4 (1977). They also demonstrated an $I_{50}$ of about 3 mg/kg p.o. in inhibiting infused angiotensin I in rats. As such, these would be very useful in the treatment of hypertension.

The compounds may be administered orally or parenterally in the treatment of hypertensions and it is within the professional judgment and skill of the practitioner to determine the amount to be administered. Suitable dosage forms include tablets, capsules, elixirs and injectables.

I claim:
1. A compound of the formula:

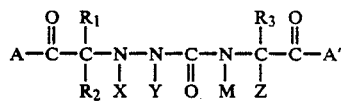

and pharmaceutically-accepted salts thereof, wherein
A and A' are independently hydroxy, lower alkoxy, lower alkenoxy, di-lower alkylamino lower alkoxy, lower acylamino lower alkoxy, lower acyloxy lower alkoxy, $C_6$–$C_{10}$ aryloxy, $C_6$–$C_{10}$ aralkyloxy, amino, lower alkanoylamino, lower alkylamino, di-lower alkylamino, hydroxyamino, or substituted $C_6$–$C_{10}$ aralkoxy wherein the substituent is lower alkyl, halo, or lower alkoxy;
$R_1$ is hydrogen; lower alkyl, lower alkenyl, lower alkynyl; $C_3$–$C_7$ cycloalkyl; $C_6$–$C_{10}$ aryl; heterocyclic; fused $C_6$–$C_{10}$ aryl-$C_3$–$C_{10}$ aralkyl; substituted lower alkyl, alkenyl or alkyl wherein the substituent is halo, hydroxy, lower alkoxy, $C_6$–$C_{10}$ aryloxy, amino, lower alkylamino, di-lower alkylamino, lower acylamino, $C_6$–$C_{10}$ arylamino, guanidino, imidazolyl, indolyl, mercapto, lower alkylthio, $C_6$–$C_{10}$ arythio, carboxy, carboxamino, or carbo lower alkoxy; substituted $C_6$–$C_{10}$ aryl wherein the substituent is lower alkyl, lower alkxoy or halo; heterocyclic lower alkyl; $C_8$–$C_{10}$ aralkenyl or heterocyclic lower alkenyl; substituted $C_7$–$C_{10}$ aralkyl, heterocyclic lower alkyl, $C_8$–$C_{10}$ aralkenyl, or heterocyclic lower allkenyl wherein the substitutent is halo, dihalo, lower alkyl, hydroxy, lower alkoxy, amino, amino lower alkyl, lower acylamio, di-lower alkylamino, lower alkylamino, carboxy, halo lower alkyl, cyano; $C_7$–$C_{10}$ aralkyl or heterocyclic lower alkyl substituted on the alkyl moiety by amino or lower acylamino;

$R_2$ and $R_3$ are independently hydrogen, lower alkyl, lower alkenyl, $C_7$–$C_{10}$ aralkyl or $C_3$–$C_7$ cycloalkyl;

M is hydrogen, lower alkyl, lower alkenyl, lower alkynyl, $C_3$–$C_7$ cycloalkyl-lower alkyl, $C_6$–$C_{10}$ aryl, $C_7$–$C_{10}$ aralkyl, heterocyclic, fused $C_6$–$C_{10}$ aryl $C_3$–$C_7$ cycloalkyl, fused $C_6$–$C_{10}$ aryl-$C_3$–$C_7$-cycloalkyl-lower alkyl, lower alkoxyalkyl, lower alkythio lower alkyl, lower alkylamino lower alkyl, di-lower alkylaminolower alkyl;

Z is hydrogen, lower alkyl, $C_3$–$C_7$ cycloalkyl, phenyl, phenyl lower alkyl, hydroxy lower alkyl, amino lower alkyl, guanidino lower alkyl, imidazolyl lower alkyl, indolyl lower alkyl, mercapto lower alkyl, or lower alkylthio lower alkyl;

M and Z when taken together form an alkylene bridge of from 2 to 4 carbon atoms; an alkylene bridge of 2 carbon atoms and one sulfur atom; an alkylene bridge of from 3 to 4 carbon atoms having a double bond; as substituted alkylene bridge of form 2 to 5 carbons in which the substituent is hydroxy, lower alkoxy; or when taken with the carbon and nitrogen to which they are respectively attached form a tetrahydroisoquinoline, dihydroindole or pyrrolidine ring;

X and Y together from an alkylene bridge of 4 carbon atoms;

wherein in the case of a heterocyclic, heterocyclic lower alkyl or heterocyclic lower alkenyl group, said group is pyridinyl, piperidinyl, pyrrolyl, pyrrolidinyl, quinolinyl, isoquinolinyl, tetrahydroquinolinyl, thiazolidinyl, thiazolinyl, thiazoyl, imidazolidinyl, imidazolinul, imidazolyl, thiophenyl, tetrahydrothiophenyl, furyl or tetrahydrofuranyl.

2. N-[Methyl-2-(1-ethoxycarbonyl-3-phenylpropyl)-hydrazinocarbonyl]-N-(5-indanyl) glycine.

3. 1-(1-Ethoxycarbonylethyl)-2-carboxymethylaminocarbonylhexahydropyridazine.

* * * * *